(12) United States Patent
Rice et al.

(10) Patent No.: US 9,997,328 B2
(45) Date of Patent: Jun. 12, 2018

(54) SYSTEM AND METHOD FOR FORMING A SEALED CHAMBER

(71) Applicant: APPLIED MATERIALS ISRAEL LTD., Rehovot (IL)

(72) Inventors: Michael R. Rice, Pleasanton, CA (US); Ron Naftali, Shoham (IL); Natan Schlimoff, Rehovot (IL); Igor Krivts (Krayvitz), Rehovot (IL); Israel Avneri, Ramat-Gan (IL); Yoram Uziel, Misgav (IL); Zvika Rozenberg, Mevaselet (IL); Erez Admoni, Petach-Tikva (IL); Yochanan Madmon, Qiryat Equron (IL)

(73) Assignee: APPLIED MATERIALS ISRAEL LTD., Rehovot (IL)

( * ) Notice: Subject to any disclaimer, the term of this patent is extended or adjusted under 35 U.S.C. 154(b) by 0 days. days.

(21) Appl. No.: 15/160,972

(22) Filed: May 20, 2016

(65) Prior Publication Data
US 2016/0268097 A1    Sep. 15, 2016

Related U.S. Application Data

(63) Continuation of application No. PCT/US2014/067329, filed on Nov. 25, 2014.
(Continued)

(51) Int. Cl.
*G01N 21/95* (2006.01)
*G02B 21/26* (2006.01)
(Continued)

(52) U.S. Cl.
CPC .......... *H01J 37/18* (2013.01); *G01N 21/9501* (2013.01); *G02B 21/26* (2013.01);
(Continued)

(58) Field of Classification Search
USPC .......................................... 118/733
See application file for complete search history.

(56) References Cited

U.S. PATENT DOCUMENTS

| | | | |
|---|---|---|---|
| 6,408,767 B1 * | 6/2002 | Binnard | F16C 29/025 108/147 |
| 7,394,076 B2 | 7/2008 | Devitt et al. | |

(Continued)

FOREIGN PATENT DOCUMENTS

| | | |
|---|---|---|
| KR | 1020090066247 A | 6/2009 |
| WO | 2015081072 A1 | 6/2015 |

OTHER PUBLICATIONS

PCT/US2014/067329, "International Search Report and Written Opinion", dated Feb. 26, 2015, 11 pages.
(Continued)

*Primary Examiner* — Karla A Moore
*Assistant Examiner* — Tiffany Z Nuckols
(74) *Attorney, Agent, or Firm* — Kilpatrick Townsend & Stockton LLP

(57) ABSTRACT

Chamber elements defining an internal chamber to be utilized during a substrate related stage selected from the group consisting of substrate manufacturing stage and substrate inspection stage, the chamber elements comprising: a first element having a first surface; a second element having a second surface about the periphery of the internal chamber; a third element connected to the second element; and a clamping mechanism that is connected to the second and third elements and is arranged to press the second element towards the first element; wherein a first area of the first surface and a second area of the second surface come into proximity with each other at a first interface; wherein the first surface is positioned above the second surface; wherein a gas groove and a vacuum groove are formed in the second area; wherein the second element comprises a gas conduit
(Continued)

that is arranged to provide gas to the gas groove and a vacuum conduit that is arranged to provide vacuum to the vacuum groove; wherein a provision of the gas and the vacuum assists in a formation of a gas cushion between the first and second areas; wherein the chamber elements are operable to partially surround a first portion of a movement system and a substrate during the substrate related stage, the movement system is arranged to introduce a movement of the first element in relation to the second element and the third element, wherein the gas cushion maintains predefined conditions in the internal chamber during the movement.

17 Claims, 8 Drawing Sheets

Related U.S. Application Data

(60) Provisional application No. 61/909,224, filed on Nov. 26, 2013.

(51) Int. Cl.
    *H01J 37/18*     (2006.01)
    *H01J 37/20*     (2006.01)
    *H01L 21/67*     (2006.01)

(52) U.S. Cl.
    CPC .......... *H01J 37/20* (2013.01); *H01L 21/6719* (2013.01); *H01L 21/67126* (2013.01); *H01L 21/67196* (2013.01); *H01L 21/67242* (2013.01); *G01N 2201/023* (2013.01); *H01J 2237/022* (2013.01); *H01J 2237/182* (2013.01); *H01J 2237/202* (2013.01)

(56) References Cited

U.S. PATENT DOCUMENTS

| | | | |
|---|---|---|---|
| 7,642,523 B1 | 1/2010 | Devitt et al. | |
| 8,123,868 B2 | 2/2012 | Devitt et al. | |
| 8,795,769 B2 | 8/2014 | Devitt et al. | |
| 2002/0110962 A1* | 8/2002 | Wada | B23K 26/032 438/158 |
| 2003/0185715 A1* | 10/2003 | Krivts | H01L 21/67126 118/730 |
| 2005/0037619 A1 | 2/2005 | Granneman et al. | |
| 2009/0002658 A1* | 1/2009 | Kiuchi | G03F 7/70733 355/53 |
| 2010/0012838 A1* | 1/2010 | Hatakeyama | G01N 23/2251 250/307 |
| 2010/0206481 A1 | 8/2010 | Gigacher et al. | |
| 2012/0067286 A1 | 3/2012 | He et al. | |
| 2013/0291905 A1 | 11/2013 | Hashizume et al. | |
| 2015/0037514 A1 | 2/2015 | Devitt et al. | |

OTHER PUBLICATIONS

PCT/US2014/067329, "International Preliminary Report on Patentability", dated Jun. 9, 2016, 6 pages.

* cited by examiner

```
┌─────────────────────────────┐          ┌─────────────────────────────┐
│ Generating an air cushion   │          │ Introducing a movement, by  │
│ between first and second    │          │ the movement system, of the │
│ areas of first and second   │          │ first element in relation to│
│ surfaces of first and second│          │ the second element and the  │
│ internal chamber elements   │          │ third element, while        │
│ by providing vacuum to a    │          │ maintaining, by the gas     │
│ vacuum groove formed within │          │ cushion, predefined         │
│ the second surface providing│          │ conditions in the internal  │
│ gas to a gas groove formed  │          │ chamber during the movement.│
│ within the first surface;   │          │                        420  │
│ wherein the first and second│          └─────────────────────────────┘
│ chamber elements and a third│
│ chamber element are operable│
│ to partially surround a     │
│ first portion of a movement │
│ system and a substrate      │
│ during the substrate related│
│ stage. 410                  │
└─────────────────────────────┘
```

SYSTEM AND METHOD FOR FORMING A SEALED CHAMBER

CROSS-REFERENCES TO RELATED APPLICATIONS

This application is a continuation of and claims priority to PCT/US2014/067329, filed Nov. 25, 2014; which claims the benefit of U.S. Provisional Patent Application No. 61/909,224, filed Nov. 26, 2013. The disclosures of each of the PCT/US2014/067329 and 61/909,224 applications are herein incorporated by reference in their entirety for all purposes.

BACKGROUND OF THE INVENTION

The present invention relates to semiconductor inspection systems and/or processing, and more particularly to chambers for processing or inspecting substrates such as semiconductor wafers, reticles, and the like for the manufacture of integrated circuits (ICs). Integrated circuits are manufactured by building semiconductor devices on one or more substrates in a process chamber. The semiconductor devices are interconnected to form the IC. A semiconductor wafer may have one, or many, or a few ICs.

Semiconductor devices are fabricated on substrates such as silicon wafers by processes that involve depositing, patterning, and removing of materials on the substrates. Deposition processes such as chemical vapor deposition (CVD) or physical vapor deposition (PVD) may be used to deposit a layer of material on a substrate. Photolithography techniques may be used to create a pattern on a layer of material to control where etching, depositing, or implanting will occur. Etch processes may be used to remove portions of a deposited layer, so that other materials may be deposited in the removed portions. Ion implantation processes may be used to change the properties of a deposited layer of material by physically bombarding and implanting dopants into the deposited layer. By using various ones of these process steps, semiconductor devices, and, thus, integrated circuits are created on the substrate.

There is a need to provide an efficient and relatively contamination free system and method for moving a substrate while maintaining predefined conditions within a first chamber in which the substrate is placed.

BRIEF SUMMARY OF THE INVENTION

There is provided a system that prevents sources of contamination from contaminating an inspected substrate. The system includes an internal chamber and a second chamber. The internal chamber can be located above the second chamber but other spatial relationships between the chambers may exist.

The substrate, during inspection or manufacturing processes, is located in the internal chamber in which predetermined conditions (contamination level, vacuum level, temperature and the like) are maintained even when the substrate is moved in relation to a housing of the internal chamber.

The movement may be introduced by a movement system (such as mechanical stage) located within the second chamber. Cables, control device and various other components can be located within the second chamber in order to reduce and even eliminate the amount of contaminating elements generated within the internal chamber. The internal chamber can be free of moving parts.

The first and second chambers can be isolated from each other by using one or more dynamic seals (e.g., gas cushions).

According to an embodiment of the invention, the internal chamber can include multiple elements such as first, second and third elements that have first, second and third surfaces respectively. The third element is connected to the second element.

A first area of the first surface and a second area of the second surface come into proximity with each other at a first interface.

One or more gas grooves and one or more vacuum grooves are formed in the second area. One of the gas grooves can feed gas at an atmospheric pressure.

The second element includes (i) one or more gas conduits that are arranged to provide gas to the one or more gas grooves and (ii) one or more vacuum conduits that are arranged to provide vacuum to the one or more vacuum grooves.

The provision of the gas and the vacuum assists in a formation of a gas cushion between the first and second areas. This gas cushion separates between the first and second areas and can also viewed as a dynamic seal or a product of a dynamic seal.

The chamber elements are operable to partially surround a first portion of a movement system and a substrate during the substrate related stage.

The movement system is arranged to introduce movement of the first element in relation to the second element and the third element, wherein the gas cushion maintains predefined conditions in the internal chamber during the movement.

The first and second surfaces may be horizontal, wherein the second plate can be positioned above the first surface.

The combination of the housing of the internal chamber and the first element can form an inner space of radial symmetry or an inner space of other geometrical properties.

The second chamber can be maintained at a higher pressure in relation to the internal chamber or at the same pressure level.

The first element has to withstand a limited load that is responsive to the pressure difference between the first and second chamber.

Contamination which is generated by the movement system (for example—XY stage, XYZ stage, R$\Theta$ stage or R$\Theta$Z stage), by bearing and from plastic cables may be prevented from reaching the internal chamber due to a positive air flow formed by the first dynamic seal. The first dynamic seal can be arranged to generate an air flow directed towards the second chamber and thus repel contamination from entering the internal chamber.

The suggested systems and methods enable building a vacuum environment for metrology and inspection application in which the substrate is separated from any source of contamination: position stage, motors cables, lubricants and others.

The suggested systems and method may provide one or more of the following advantages: (i) high serviceability both for the semiconductor substrates in the vacuum chamber and mechanisms that are situated in the atmospheric side, (ii) high reliability of the substrate handling process and (iii) high safety level of the chamber motion process both in the vertical and horizontal directions.

In the following figures there are provided non-limiting examples of the first, second and third elements mentioned above.

Any combinations of any of the components of any of the figures can be provided. Any combination of any of the mentioned above systems can be provided.

BRIEF DESCRIPTION OF THE DRAWINGS

The subject matter regarded as the invention is particularly pointed out and distinctly claimed in the concluding portion of the specification. The invention, however, both as to organization and method of operation, together with objects, features, and advantages thereof may best be understood by reference to the following detailed description when read with the accompanying drawings in which:

FIG. 7 illustrates a method according to an embodiment of the invention; and

Figure 1:
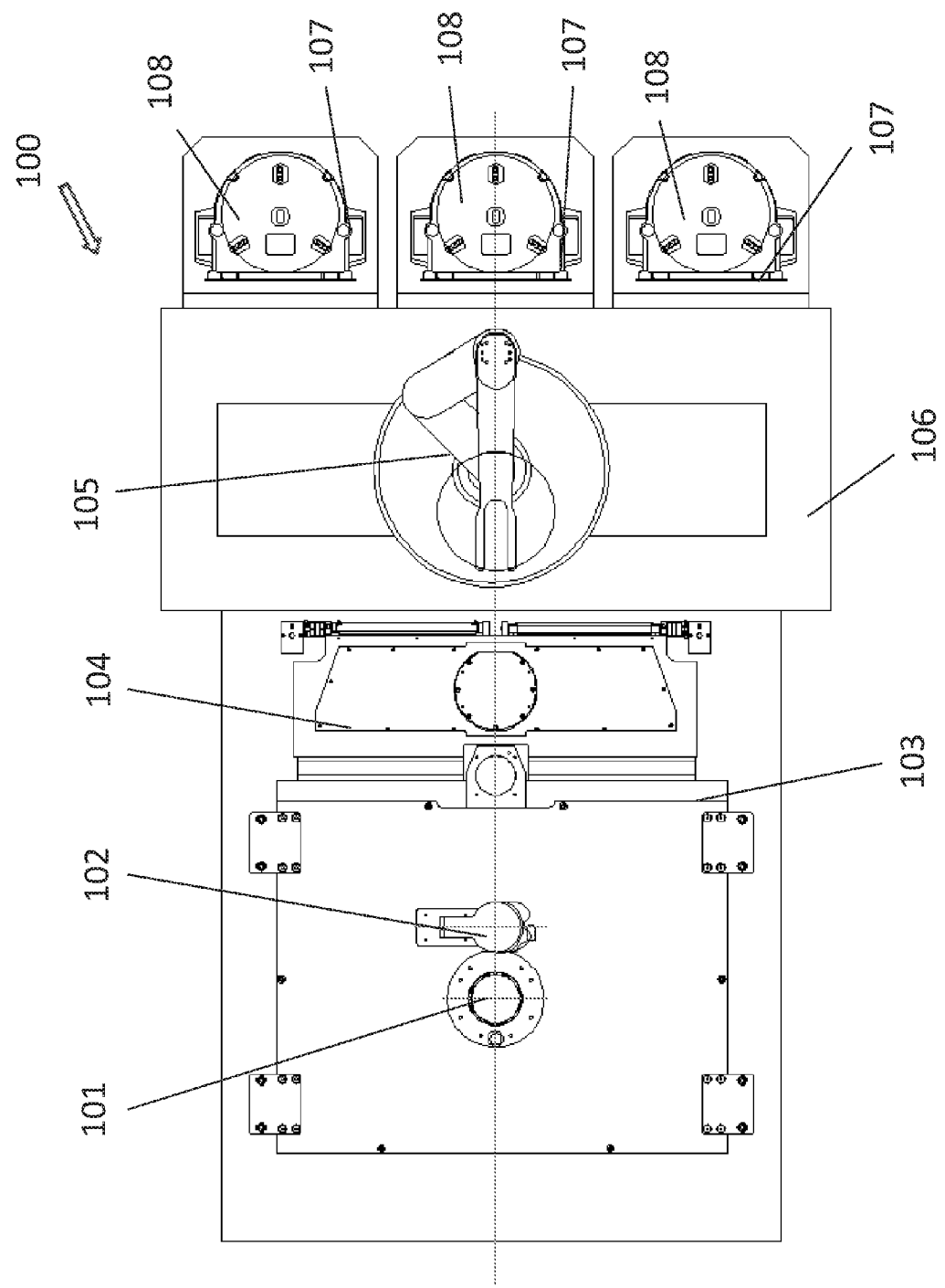
FIG. 1 is a top view of a stand-alone tool, according to an embodiment of the invention.

It will be appreciated that for simplicity and clarity of illustration, elements shown in the figures have not necessarily been drawn to scale. For example, the dimensions of some of the elements may be exaggerated relative to other elements for clarity. Further, where considered appropriate, reference numerals may be repeated among the figures to indicate corresponding or analogous elements.

DETAILED DESCRIPTION OF THE INVENTION

In the following detailed description, numerous specific details are set forth in order to provide a thorough understanding of the invention. However, it will be understood by those skilled in the art that the present invention may be practiced without these specific details. In other instances, well-known methods, procedures, and components have not been described in detail so as not to obscure the present invention.

The subject matter regarded as the invention is particularly pointed out and distinctly claimed in the concluding portion of the specification. The invention, however, both as to organization and method of operation, together with objects, features, and advantages thereof, may best be understood by reference to the following detailed description when read with the accompanying drawings.

It will be appreciated that for simplicity and clarity of illustration, elements shown in the figures have not necessarily been drawn to scale. For example, the dimensions of some of the elements may be exaggerated relative to other elements for clarity. Further, where considered appropriate, reference numerals may be repeated among the figures to indicate corresponding or analogous elements.

Because the illustrated embodiments of the present invention may, for the most part, be implemented using electronic components and modules known to those skilled in the art, details will not be explained in any greater extent than that considered necessary as illustrated above, for the understanding and appreciation of the underlying concepts of the present invention and in order not to obfuscate or distract from the teachings of the present invention.

The assignment of the same reference numbers to various components may indicate that these components are similar to each other.

FIG. 1 is a top view of a stand-alone tool 100, according to an embodiment of the invention. The stand-alone tool 100 performs substrate related processes such as manufacturing and/or inspecting the substrate. According to an embodiment of the invention, tool 100 includes a Scanning Electron Microscope (SEM) column 101, optical microscope 102, internal chamber intermediate element 103, load lock 104, transfer robot 105 which is installed in factory interface unit 106, wafer cassettes 107 with wafers (substrates) 108.

Figure 2:
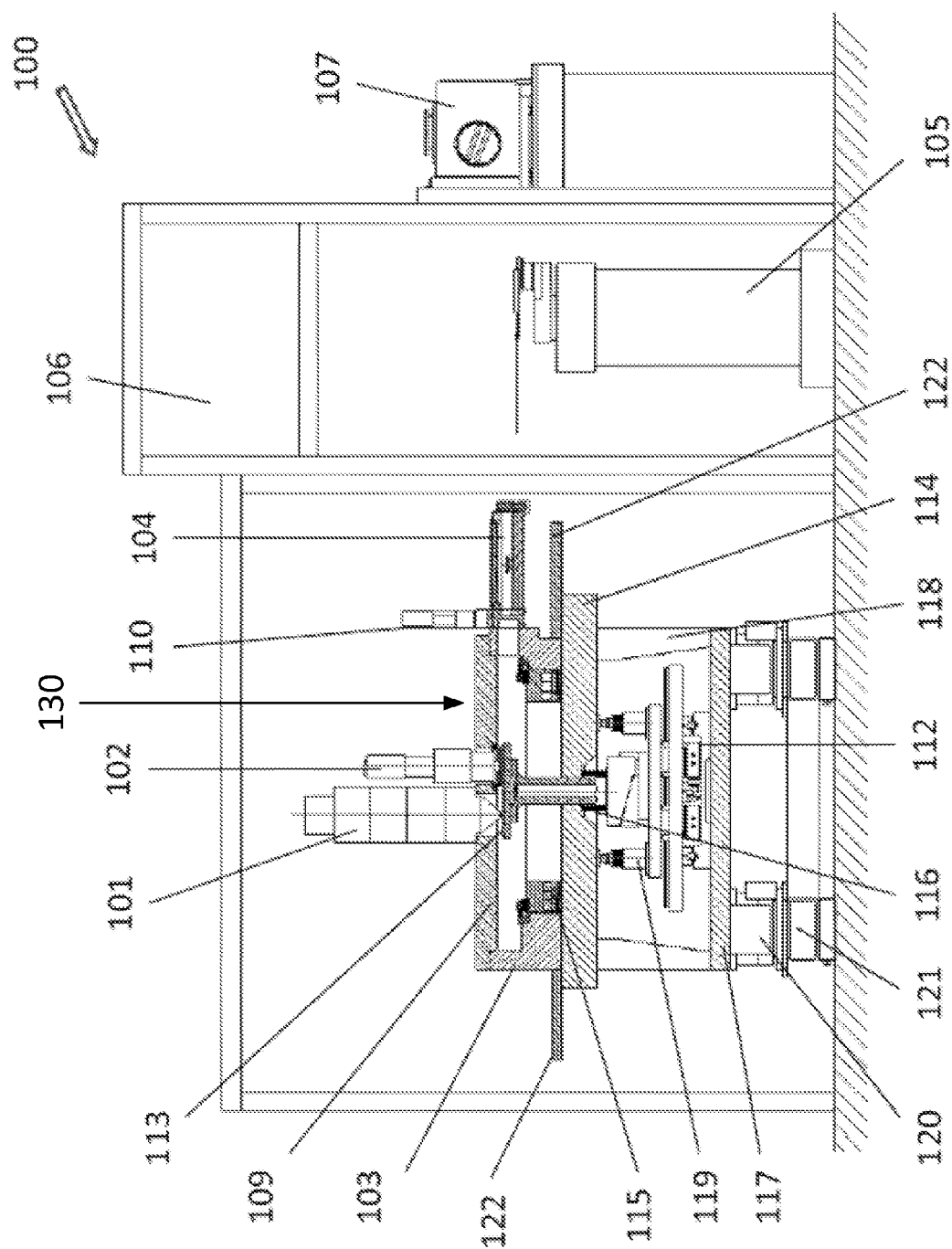
FIG. 2 is a cross sectional view of the stand-alone tool of FIG. 1 according to an embodiment of the invention.

FIG. 2 is a cross sectional view of the stand-alone tool 100 according to an embodiment of the invention.

The stand-alone tool includes an internal chamber 130 that is formed multiple chamber elements. The multiple chamber elements include a first element (such as sealing plate 114), a second element (such as an air bearing/differential pumping (AB/DP) insert 115), a third element (such as an internal chamber intermediate element 103), and an internal chamber cover 109.

FIG. 2 illustrates internal chamber cover 109, internal gate 110, external gate (not shown) for allowing gas to enter the tool, XYZ-stage 112, substrate chuck 113, a first element such as sealing plate 114 (having a first area that is denoted 114' in FIG. 4), a second element such as air bearing/differential pumping (AB/DP) insert 115 (having a second area that is denoted 115' in FIG. 5), sealing bellows 116, XYZ-stage plate 117 with stage plate supports 118, sealing plate supports 119, vibration isolation system 120, chassis 121, an upper plate 200 of a Y-axis stage, and screens 122.

The SEM column 101 and optical microscope 102 are mounted on the internal chamber cover 109 such as to inspect substrates (not shown) located within the internal chamber 130. In operation, transfer robot 105 picks up a substrate from the wafer cassette 107 and loads the substrate 108 (not shown in FIG. 2) into the load lock 104.

The transfer robot 105 is located into factory interface unit 106 that provides the clean transfer process of the substrates 108 from cassettes 107 to load lock 104. The internal transfer unit (not shown in FIG. 2) picks up a substrate (not shown in FIG. 2) from the load lock 104 and loads the substrate on the substrate chuck 113. The substrate chuck 113 holds the substrate during a manufacturing stage and/or inspection stage. The substrate chuck 113 hold the substrate by using electrostatic, mechanical or others means.

The internal gate 110 and the external gate (not shown) provide the special cycle of the pumping and venting process of the load lock 104. The XYZ position stage 112 moves the substrate under SEM and optical microscope in the 3-degrees freedom. The XYZ position stage 112 mounts of the XYZ-stage plate 117, which is connected to the internal chamber 130 with stage plate supports 118.

The sealing plate 114, AB/DM insert 115 and sealing bellows 116 provide a dynamic vacuum seal (gas cushion) of the internal chamber during the substrate 108 motion by XYZ position stage 112 in the 3-degrees freedom.

The vibration isolation system 120 and chassis 121 are intended to support the whole mechanical platform.

It is important to note that as an example, according to FIG. 2 the horizontal movement of the sealing plate 114 is provided by the sealing plate supports 119, however the sealing plate motion may be performed by separate actuators, which can be mounted between the sealing plate 114 and the XYZ position stage 112, or between the sealing plate and internal chamber 130 (not shown in FIG. 2).

The screens 122 that are mounted around of the internal chamber 130 are intended for protection of the sealing plate 114 form particles.

In the example of FIG. 2, the sealing plate 114 is mounted on the three sealing plate supports 119 (note that a different structure and a different number of sealing plate supports is applicable). The cross section view of the sealing plate support 119, which is mounted on the upper plate 200 of the Y-stage, is shown in FIG. 3.

Figure 3:
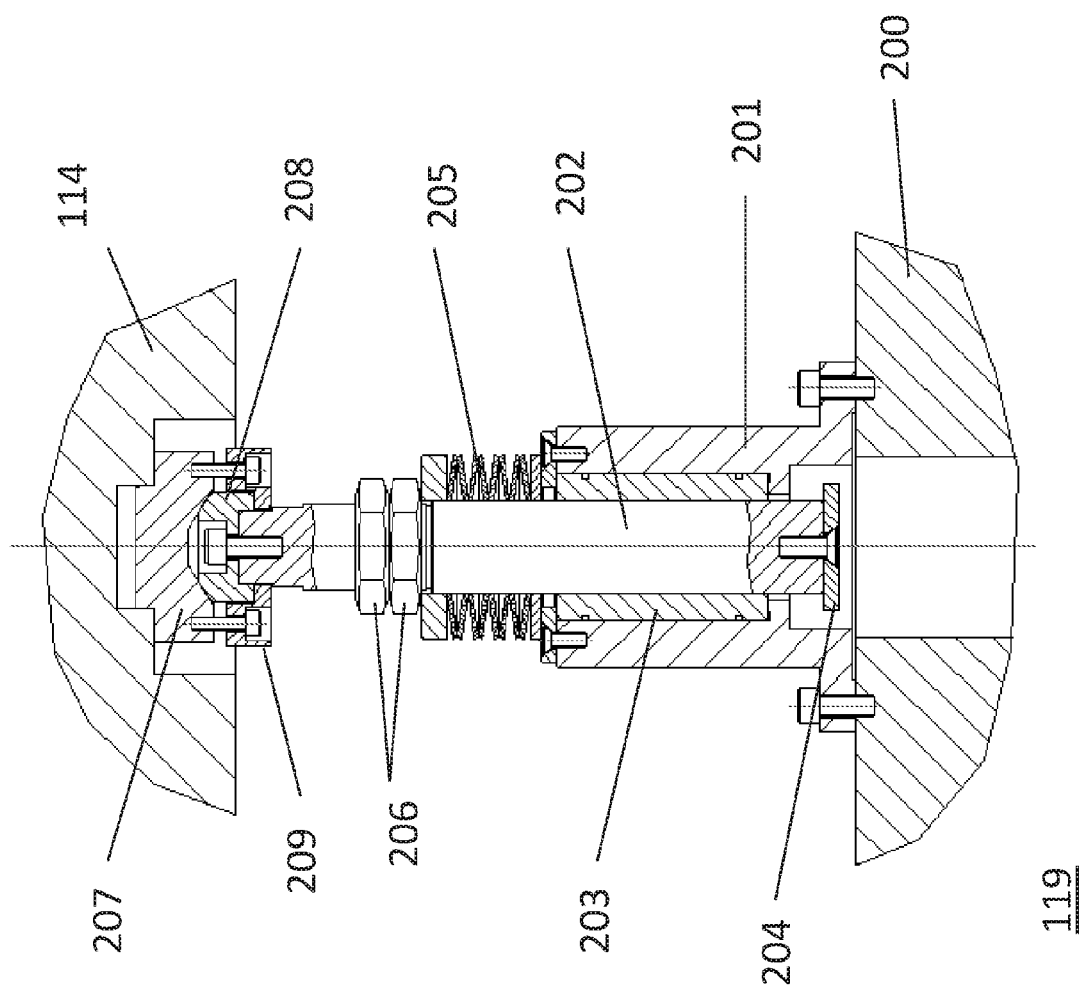
FIG. 3 is a cross sectional view of a sealing plate support and its surroundings according to an embodiment of the invention.

FIG. 3 is a cross sectional view of a sealing plate support (e.g. element 119 shown in FIG. 2) and its surroundings according to an embodiment of the invention.

Each sealing plate support 119 includes housing 201, rod 202, slide bushing 203 (the standard slide bushings type TK or GM by "NB" may be used), hard stop 204, disk springs 205 and adjusting nuts 206.

The clamping flange 209, the spherical cap 208 and support bushing 207 may provide a kinematic joint between the rod 202 and sealing plate 114 that allows three-dimensional movement (3 degrees of freedom) between the sealing plate 114 and the sealing plate support. The non-flat (curved, concaved or polygon) surfaces of the support bushing and the spherical cap facilitate three dimensional movement.

The sealing plate supports 119 with kinematic joint provide the accurate vertical and horizontal motion of the sealing plate 114. In this case the preload of the disk springs 205 should provide the floating support of the sealing plate 114 because the gap between sealing plate 114 and AB/DV insert 115 comes out as result of the force balance between air bearing and vacuum.

As discussed above, the XYZ position stage 112 is mounted outside of the chamber 130. This feature decreases the potential of contaminating the interior of the chamber 130. Various contaminants, for example, different kinds of polymers, may be formed in the chamber by a process of carbonization when hydrocarbon molecules from grease, adhesive, or insulation of wires or connectors would have been dissociated during either processing or inspection of a substrate inside the chamber, should the XYZ position stage 112 was mounted inside of chamber 130.

Figure 4:
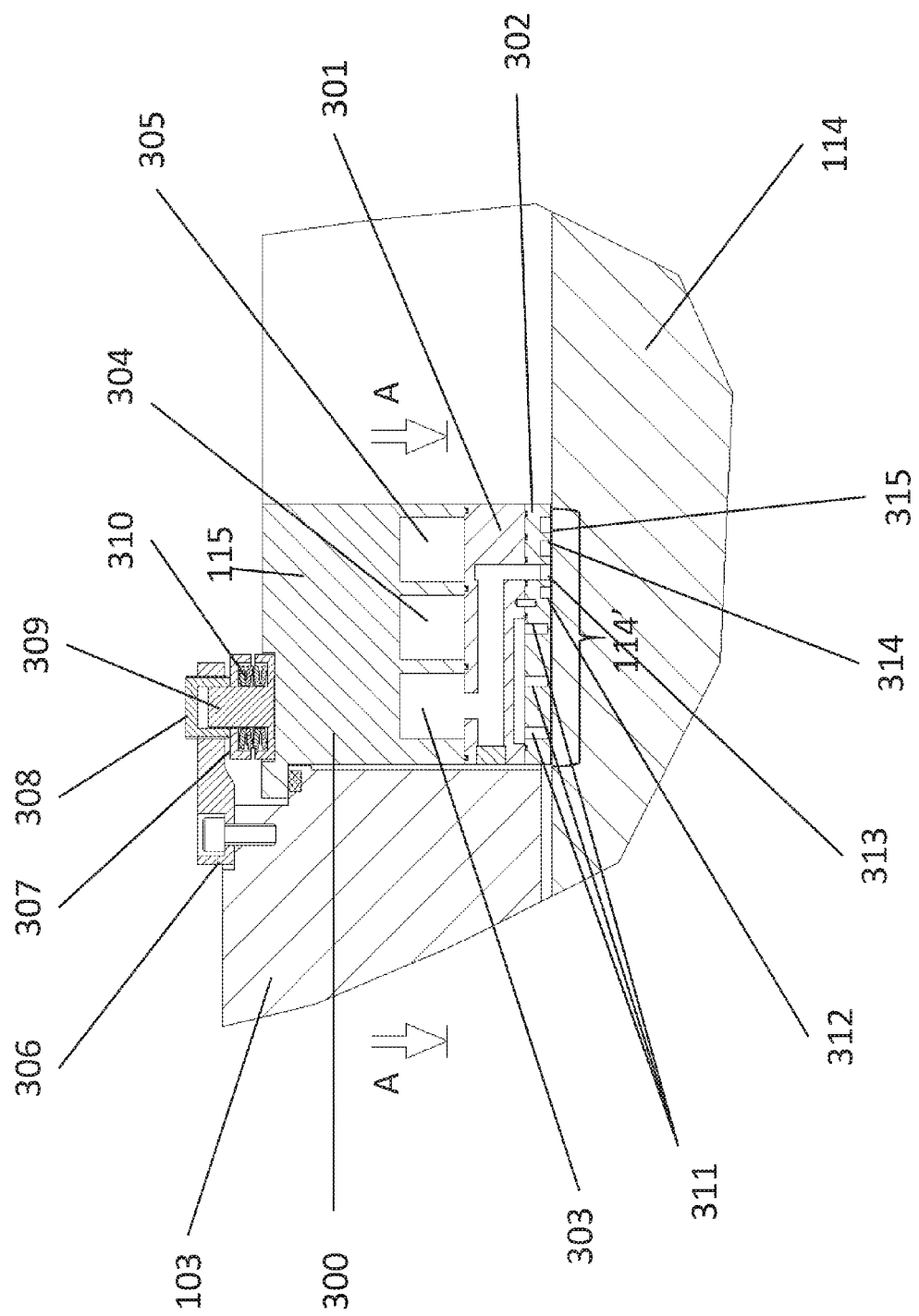
FIG. 4 is a cross sectional view of some internal chamber elements that illustrates a dynamic seal according to an embodiment of the invention.

FIG. 4 is a cross sectional view of the area of insert 115 (illustrated in FIG. 2) that illustrates a dynamic seal according to an embodiment of the invention.

In the example shown in FIG. 4, the AB/DP insert 115 is mounted in the internal chamber 130 and forms a dynamic seal between bottom surface of the AB/DP insert 115 and sealing plate 114. According to an embodiment of the invention, the AB/DP insert 115 may include three major parts: upper plate 300, middle plate 301 and bottom plate 302. This partition is not mandatory and the AB/DP insert can include a single part, two parts or more than three parts that include gas and vacuum conduits and grooves.

The upper plate 300 includes three vacuum conduits 303, 304 and 305, each of which is connected with its vacuum pump (not shown in figure).

The bottom plate 302 includes the three vacuum grooves 313, 314 and 315 and atmospheric pressure gas groove 312 which is a differential pumping unit. In addition, the bottom plate 302 may include several orifices 311 which form an air bearing unit. All three plates must be hermetically interconnected. The manner in which a gas cushion (dynamic seal) is formed is illustrated, for example, in U.S. Pat. No. 6,899,765 which is incorporated herein by reference. Different conduits can provide gas at different pressure and/or vacuum levels.

The middle plate 301 is a manifold that includes (i) a first intermediate conduit 303 that provides vacuum from first vacuum conduit 303 to first vacuum groove 313, (ii) a second intermediate vacuum conduit (not shown in figure) that provides vacuum from second vacuum conduit 304 to second vacuum groove 314 (not shown in figure), (iii) a third intermediate vacuum conduit (not shown in figure) that provides vacuum from the third vacuum conduit 305 to the third vacuum groove 315 (not shown in figure), (iv) an atmospheric pressure gas conduit (not shown) that supplies, to first gas groove 312, gas at an atmospheric pressure (not shown in figure), (v) a second gas conduit (not shown) that supplies compressed gas to air bearings orifices 311.

The AB/DP insert 115 is connected to the internal chamber intermediate element 103 by a clamping mechanism which comprise a bracket 306, adjusting nut 308, base 309, thrust washer 307 and disk springs 310. These clamping mechanisms are arranged around the perimeter of insert 115 and are adapted to provide sufficient force to compensate for the force of the pressure differential between the AB/DP insert 115 and the atmosphere.

Figure 5:
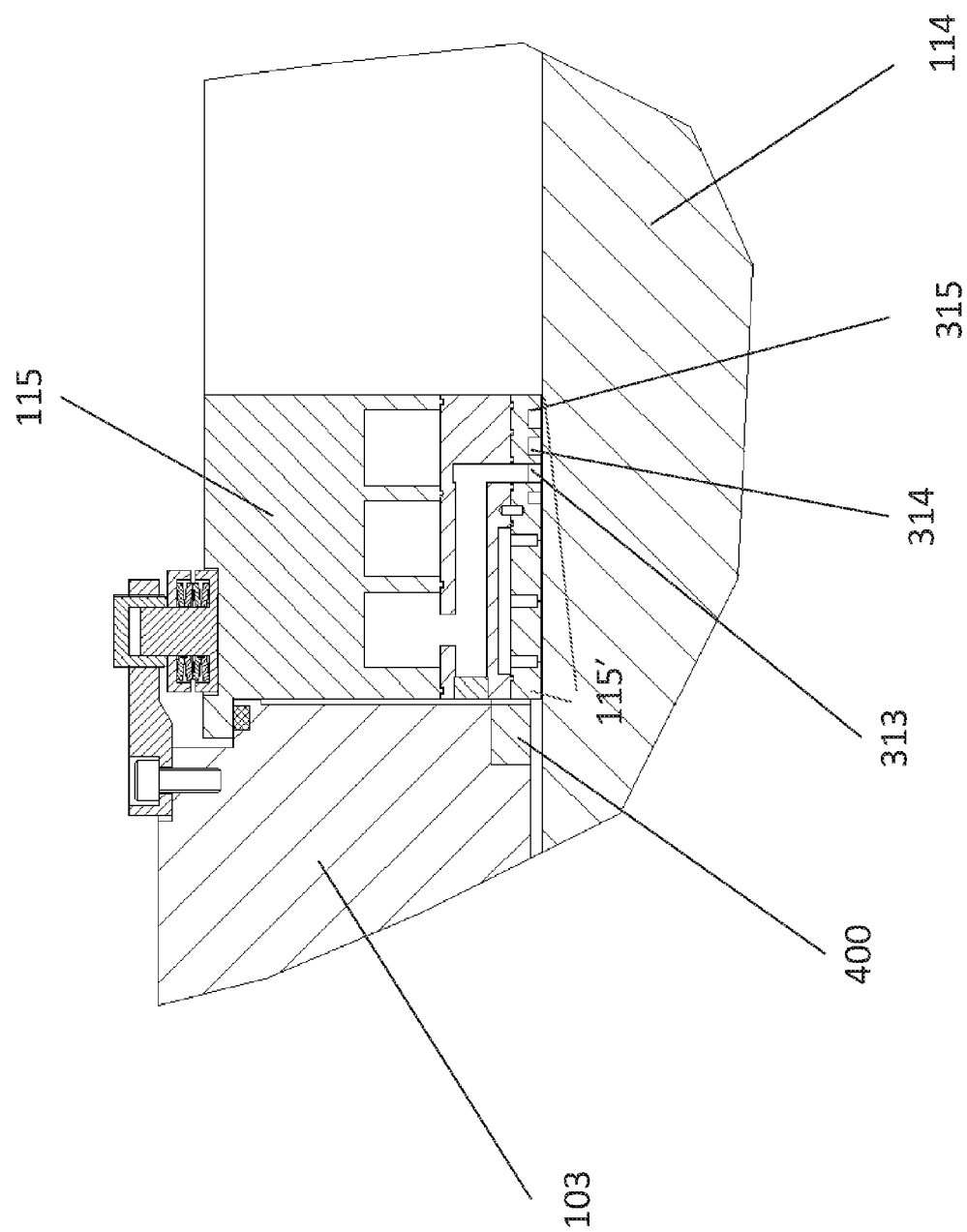
FIG. 5 is a cross sectional view of some internal chamber elements that illustrates a dynamic seal according to an embodiment of the invention.

FIG. 5 is a cross sectional views of the area of insert 115 (illustrated in FIG. 2) that illustrates dynamic seals according to an embodiment of the invention.

To more robustly prevent the penetration of the molecular contaminants the excimer lamp may be use. FIG. 5 schematically shows such option where the UV excimer lamp 400 is mounted around the AB/CD insert 115—within a space formed in the internal chamber intermediate element 103. The UV excimer lamp 400 emits ultraviolet light which is greatly absorbed by oxygen so that high concentration active oxygen can be generated. The ultraviolet light is capable of breaking the organic molecular bonds and so provides benefits in various processes by accelerating the cleaning speed, improving the quality of cleaning and boosting the product yield.

Optical cleaning is an efficient cleaning method for eliminating contaminants that wet type cleaning cannot remove material where wet cleaning is not usable or materials easily damaged by heat.

Figure 8:
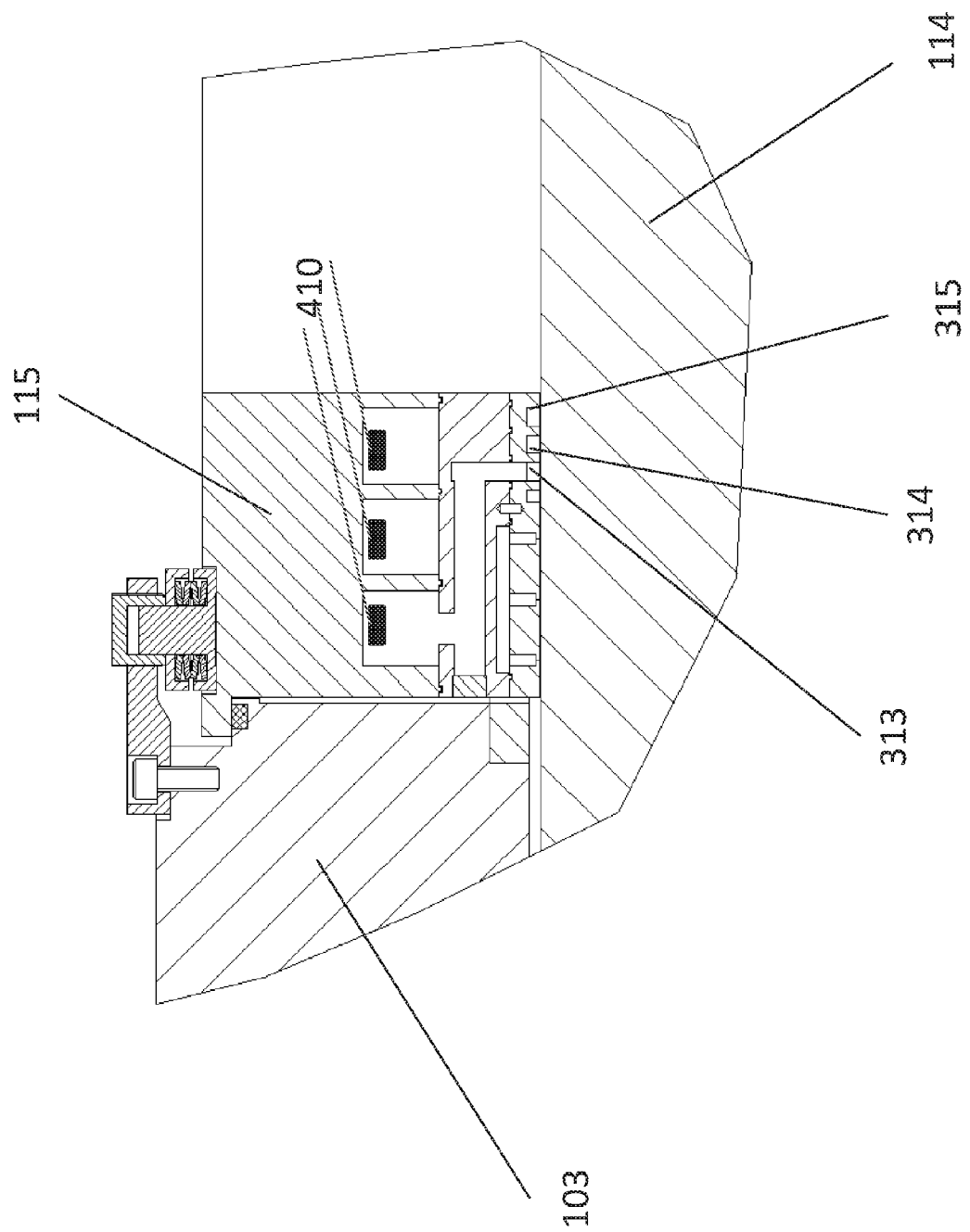
FIG. 8 is a cross sectional view of some internal chamber elements that illustrates a dynamic seal according to an embodiment of the invention.

Another cleaning approach involves the use of plasma. In this case, as illustrated in FIG. 8, in differential pump vacuum grooves 313, 314 and 315 may be generate a plasma (electrodes 410 for generating plasma are illustrated in FIG. 8), which is capable to brake the organic molecules that come with gas via air bearing gap or on the sealing plate surface. Also this process provides high quality of cleaning. Cold plasma can be generated by electrodes inserted in the vacuum grooves and adapted to provide plasma.

Figure 6:
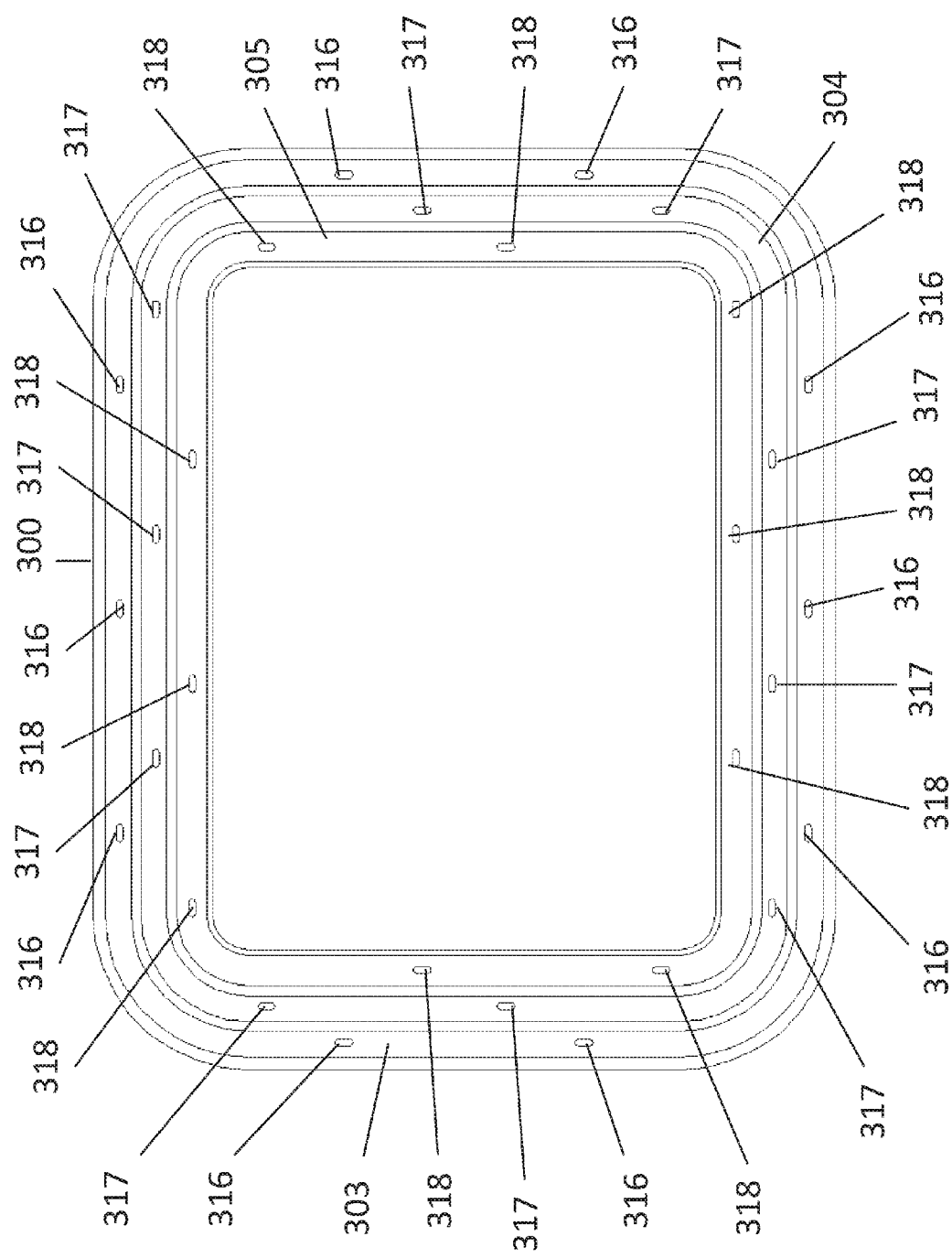
FIG. 6 illustrates some of the gas conduits and gas grooves according to an embodiment of the invention.

FIG. 6 illustrates some of the gas conduits and gas grooves according to an embodiment of the invention.

FIG. 6 illustrates the section A-A in FIG. 4. As illustrated in FIG. 4, the AB/DP insert 115 includes three concenters triplets of the suction subsystem 300. First triplet contains the vacuum conduit 303, vacuum channels 316 and vacuum groove (denoted 313 in FIG. 5—is located below section A-A and not shown in FIG. 6). Second one has vacuum conduit 304, vacuum channels 317 and vacuum grove (denoted 314 in FIG. 5—is located below section A-A and not shown in FIG. 6). Third triplet includes of the vacuum conduit 305, vacuum channels 318 and vacuum groove (denoted 315 in FIG. 5—is located below section A-A and not shown in FIG. 6). Each triplet is connected to a vacuum pump (not shown in figures) that sucks the gas from the triplet to provide a desired vacuum level at the vacuum groove.

FIG. 7 illustrates method 400 according to an embodiment of the invention.

Method 400 may be executed by any of the systems, tools and chamber elements illustrated in the previous figures. The method maintains predefined conditions within an internal chamber to be utilized during a substrate related step selected from the group consisting of substrate manufacturing step and substrate inspection step.

Method 400 includes steps 410 and 420.

Step 410 includes generating an air cushion between first and second areas of first and second surfaces of first and second internal chamber elements by providing vacuum to a vacuum groove formed within the second surface providing gas to a gas groove formed within the first surface; wherein the first and second chamber elements and a third chamber element are operable to partially surround a first portion of a movement system and a substrate during the substrate related step.

Step 420 includes introducing a movement, by the movement system, of the first element in relation to the second element and the third element, while maintaining, by the gas cushion, predefined conditions in the internal chamber during the movement.

Any arrangement of components to achieve the same functionality is effectively "associated" such that the desired functionality is achieved. Hence, any two components herein combined to achieve a particular functionality can be seen as "associated with" each other such that the desired functionality is achieved, irrespective of architectures or intermedial components. Likewise, any two components so associated can also be viewed as being "operably connected," or "operably coupled," to each other to achieve the desired functionality.

Furthermore, those skilled in the art will recognize that boundaries between the above described operations merely illustrative. The multiple operations may be combined into a single operation, a single operation may be distributed in additional operations and operations may be executed at least partially overlapping in time. Moreover, alternative embodiments may include multiple instances of a particular operation, and the order of operations may be altered in various other embodiments.

Other modifications, variations and alternatives are also possible. The specifications and drawings are, accordingly, to be regarded in an illustrative rather than in a restrictive sense.

In the claims, any reference signs placed between parentheses shall not be construed as limiting the claim. The word 'comprising' does not exclude the presence of other elements or steps then those listed in a claim. Furthermore, the terms "a" or "an," as used herein, are defined as one or more than one. Also, the use of introductory phrases such as "at least one" and "one or more" in the claims should not be construed to imply that the introduction of another claim element by the indefinite articles "a" or "an" limits any particular claim containing such introduced claim element to inventions containing only one such element, even when the same claim includes the introductory phrases "one or more" or "at least one" and indefinite articles such as "a" or "an." The same holds true for the use of definite articles. Unless stated otherwise, terms such as "first" and "second" are used to arbitrarily distinguish between the elements such terms describe. Thus, these terms are not necessarily intended to indicate temporal or other prioritization of such elements. The mere fact that certain measures are recited in mutually different claims does not indicate that a combination of these measures cannot be used to advantage.

While certain features of the invention have been illustrated and described herein, many modifications, substitutions, changes, and equivalents will now occur to those of ordinary skill in the art. It is, therefore, to be understood that the appended claims are intended to cover all such modifications and changes as fall within the true spirit of the invention.

What is claimed is:

1. Chamber elements defining an internal chamber to be utilized during a substrate processing or substrate inspection stage, the chamber elements comprising:
    a first element having a first surface;
    a second element having a second surface about the periphery of the internal chamber;
    a third element, separate from the first element and separate from the second element, and connected to the second element;
    a clamping mechanism that is connected to the second and third elements and is arranged to press the second element towards the first element;
    a movement system; and
    an ultraviolet radiation source that is arranged to direct ultraviolet radiation towards the first surface and positioned adjacent to the third element within a space formed between the third element and the first element;
    wherein a first area of the first surface and a second area of the second surface come into proximity with each other at a first interface; wherein the first surface is positioned above the second surface;
    wherein a gas groove and a vacuum groove are formed in the second area;
    wherein the second element comprises a gas conduit that is arranged to provide gas to the gas groove and a vacuum conduit that is arranged to provide vacuum to the vacuum groove; wherein a provision of the gas and the vacuum assists in a formation of a gas cushion between the first and second areas;
    wherein the chamber elements are operable to partially surround a first portion of the movement system and a substrate during the substrate processing or inspection stage, the movement system is arranged to introduce a movement of the first element in relation to the second element and the third element, wherein the gas cushion maintains predefined conditions in the internal chamber during the movement.

2. The chamber elements according to claim 1 wherein the third element forms a part of a housing of the internal chamber; wherein the third element has a third surface that is parallel to the second surface; wherein a distance between the third surface and the first surface exceeds a distance between the second surface and the first surface.

3. The chamber elements according to claim 1 wherein multiple gas grooves and multiple vacuum grooves are formed in the second area; wherein the second element comprises multiple gas conduits that are arranged to provide gas to the multiple gas grooves and multiple vacuum conduits that are arranged to provide vacuum to the multiple vacuum grooves; wherein the provision of the gas and the vacuum assists in the formation of the gas cushion between the first and second areas.

4. The chamber elements according to claim 3 wherein multiple gas conduits are formed above the second surface.

5. The chamber elements according to claim 3 wherein a cross section of each one of the multiple gas conduits exceeds a cross section of each one of the vacuum grooves.

6. The chamber elements according to claim 3 wherein the gas conduits, the vacuum conduits, the gas grooves and the vacuum grooves are annular.

7. The chamber elements according to claim 1 further a plasma source that is arranged to provide plasma to the vacuum groove.

8. The chamber elements according to claim 1 wherein the first element is movably coupled to a first element support thereby allowing a three-dimensional movement between the first element and the first support element.

9. The chamber elements according to claim 1 wherein the vacuum groove comprises electrodes for generating plasma in the gas groove.

10. The chamber elements according to claim 1 comprising multiple spaced apart clamping mechanisms, each clamping mechanism is connected to the second and third element and is arranged to press the second element towards the first element.

11. The chamber elements according to claim 1 wherein the first element is a sealing plate and wherein the second element is an air bearing insert.

12. Chamber elements defining an internal chamber to be utilized during a substrate processing or substrate inspection stage, the chamber elements comprising:
a first element having a first surface;
a second element having a second surface about the periphery of the internal chamber;
a third element, the third element being separate from the first element, separate from the second element and connected to the second element; and
a clamping mechanism that is connected to the second and third elements and is arranged to press the second element towards the first element;
wherein a first area of the first surface and a second area of the second surface come into proximity with each other at a first interface; wherein the first surface is positioned above the second surface;
wherein a gas groove and a vacuum groove are formed in the second area;
wherein the second element comprises a gas conduit that is arranged to provide gas to the gas groove and a vacuum conduit that is arranged to provide vacuum to the vacuum groove; wherein a provision of the gas and the vacuum assists in a formation of a gas cushion between the first and second areas;
wherein the chamber elements are operable to partially surround a first portion of a movement system and a substrate during the substrate processing or inspection stage, the movement system is arranged to introduce a movement of the first element in relation to the second element and the third element, wherein the gas cushion maintains predefined conditions in the internal chamber during the movement;
wherein the clamping mechanism comprises a static mechanical module that is connected to the third element, a spring and a second element interface, wherein the spring is connected between the second element interface and the static mechanical module.

13. An apparatus for inspecting substrates, the apparatus comprising:
a housing having a cover, a sealing plate spaced apart from the cover and a sidewall element, separate from the cover and from the sealing plate, that extends between the cover and the sealing plate, wherein the cover, sealing plate and sidewall element combine to form a chamber that includes a substrate inspection region and the sealing plate has a substantially planar sealing surface about a periphery of the chamber;
an air bearing insert positioned adjacent to and surrounded by the sidewall element, the air bearing insert having a lower surface spaced apart from the sealing surface of the sealing plate, a vacuum groove that opens to the sealing surface, a vacuum conduit fluidly coupled to the vacuum groove, a gas groove that opens to the sealing surface and is fluidly separate from the vacuum groove, and a gas conduit that is fluidly coupled to the gas groove;
a clamp that couples the air bearing insert to the sidewall element, the clamp being arranged to press the air bearing insert towards the sealing plate such that the lower surface and the sealing surface come into proximity with each other at a first interface;
a substrate support having a support plate configured to support a substrate within the substrate inspection region and a pedestal coupled to the substrate support plate that extends through an opening in the sealing plate;
an XYZ movement stage operatively coupled to move the sealing plate and substrate support in relation to the cover and the sidewall element a substrate positioned on the support in the X, Y and Z dimensions.

14. The apparatus set forth in claim 13 further comprising a gas source operatively coupled to provide gas to the gas groove and a vacuum pump operatively coupled to create a vacuum at the gas groove; wherein the gas source, gas groove, vacuum pump and vacuum grove being configured to form a gas cushion at the first interface between the sealing surface of the sealing plate and the lower surface of the air bearing.

15. The apparatus set forth in claim 13 further comprising scanning electron microscope and an optical microscope; and wherein the cover includes a first opening through which the scanning electron microscope can be operatively coupled to the chamber and a second opening through which the optical microscope can be operatively coupled to the chamber.

16. The apparatus set forth in claim 13 further comprising bellows configured to provide a seal between the pedestal and the sealing plate.

17. The apparatus set forth in claim 13 wherein the housing includes an opening between the cover and the sealing plate, the opening configured to receive substrates transferred into the chamber from a load lock area.

* * * * *